United States Patent [19]

Nakagawa et al.

[11] Patent Number: 4,659,722

[45] Date of Patent: Apr. 21, 1987

[54] BACTERICIDAL N-(2,2,2 TRICHLOROETHYL)PYRIDINECARBOXAMIDES

[75] Inventors: Taizo Nakagawa, Ohmiya; Eiichi Tanaka, Yono; Kengo Koike; Hiromi Yoshida, both of Ageo; Hiroshi Yoshida, Urawa, all of Japan

[73] Assignee: Nippon Kayaku Kabushiki Kaisha, Tokyo, Japan

[21] Appl. No.: 761,169

[22] Filed: Aug. 1, 1985

[30] Foreign Application Priority Data

Aug. 20, 1984 [JP] Japan .................. 59-171522
Jan. 22, 1985 [JP] Japan .................... 60-8518
Jan. 28, 1985 [JP] Japan .................. 60-12497

[51] Int. Cl.$^4$ ............... A61K 31/44; C07D 213/81; C07D 213/82; C07D 401/12
[52] U.S. Cl. .................. 514/332; 514/335; 514/336; 514/354; 514/355; 546/261; 546/262; 546/283; 546/284; 546/316; 546/323
[58] Field of Search ............ 546/316, 323, 283, 284, 546/261, 262; 514/335, 332, 336, 354, 355; 564/185

[56] References Cited

U.S. PATENT DOCUMENTS 4,294,835 10/1981 Nakagawa et al. .......... 560/16

Primary Examiner—Henry R. Jiles
Assistant Examiner—Dale A. Bjorkman
Attorney, Agent, or Firm—Henry C. Nields

[57] ABSTRACT

Disclosed is the compound of the formula:

$$R_1CONHCH-X-R_2 \atop | \atop CCl_3 \qquad (1)$$

wherein X is oxygen, sulfur or

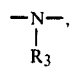

$R_1$ is 3-pyridyl or 4-pyridyl, $R_2$ is $C_1 \sim C_{12}$-alkyl; $C_3$- or $C_4$-alkenyl; $C_5$- or $C_6$-cycloalkyl which may be substituted by $C_1$- or $C_2$-alkyl; pyridyl; pyridylmethyl; phenethyl cyanoalkyl having 1 or 2 carbon atoms; methoxyethyl; 1-methylmethoxypropyl; phenyl; phenyl which is substituted by one or more of $C_1 \sim C_4$-alkyl, $C_1 \sim C_4$-alkoxy, nitro, halogen, trifluoromethyl, allyl and methoxycarbonyl; benzyl; benzyl which is substituted by one or more of methyl, nitro, methoxy and chloro; α-methylbenzyl; $C_1 \sim C_6$-alkyl which is substituted by halogen when X is oxygen or

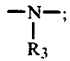

$C_2$- or $C_3$-alkyl which is substituted by dimethylamino, furfuryl or thienylmethyl; $R_3$ is hydrogen, $C_1 \sim C_4$-alkyl, cyanomethyl, methoxycarbonylmethyl, or 1-propoxycarbonylmethyl. These compounds are bactericides.

11 Claims, No Drawings

BACTERICIDAL N-(2,2,2 TRICHLOROETHYL)PYRIDINECARBOXAMIDES

DETAILED DESCRIPTION OF THE INVENTION

The present invention relates to new pyridine compounds of the formula:

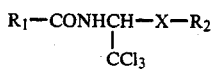 (1)

wherein
X is oxygen, sulfur or

, $R_1$ is 3-pyridyl or 4-pyridyl,
$R_2$ is $C_1 \sim C_{12}$-alkyl; $C_3$ or $C_4$-alkenyl; $C_5$ or $C_6$-cycloalkyl which may be substituted by $C_1$ or $C_2$-alkyl; pyridyl; pyridylmethyl; phenethyl; cyanoalkyl having 1 or 2 carbon atoms; methoxyethyl; 1-methoxymethylpropyl; phenyl; phenyl which is substituted by one or more of $C_1 \sim C_4$-alkyl, $C_1 \sim C_4$-alkoxy, nitro, halogen, ytrifluoromethyl, allyl and methoxycarbonyl; benzyl; benzyl which is substituted by one or more of methyl, nitro, methoxy and chloro; α-methylbenzyl; $C_1 \sim C_6$-alkyl which is substituted by halogen when X is oxygen or

;

$C_2$ or $C_3$-alkyl which is substituted by dimethylamino, furfuryl or thienylmethyl;
$R_3$ is hydrogen, $C_1 \sim C_4$-alkyl, cyanomethyl, methoxycarbonylmethyl or 1-propoxycarbonylethyl, a process for producing said compounds and their use as plant bactericides.

Plant bactericides used heretofore include copper-containing ones, organonickel compounds and antibiotics.

These plant bactericides have defects that their effectiveness for controlling bacterial leaf blight of rice, citrus canker, soft rot of vegetables, etc. are insufficient and many of them are phytotoxic to crops.

The present invention provides agricultural and horticultural bactericides having a high controlling effect and free of the defect, i.e. phytotoxicity, of the bactericides used in the prior art.

The inventors have found that when a novel compound of the above formula (I) is used, an agricultural and horticultural bactericide having a high controlling effect and free of the phytotoxicity can be obtained.

The compound of the formula (I) of the present invention may be obtained as follows:

According to a process described in Chem. Abstr. 50, 8745e (1956), a nicotinamide or isonicotinamide of the formula:

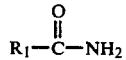 (II)

wherein $R_1$ is as defined above, is reacted with chloral at 30° to 150° C. preferably in an inert solvent to form N-(1-hydroxy-2,2,2-trichloroethyl)nicotinamide or N-(1-hydroxy-2,2,2-trichloroethyl)isonicotinamide of the formula:

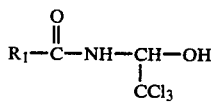 (III)

wherein $R_1$ is as defined above.

Then, a compound of the formula (III) is reacted with a halogenating agent at 15° to 100° C. preferably in an inert solvent to obtain an N-(1-halogeno-2,2,2-trichloroethyl)nicotinamide or N-(1-halogeno-2,2,2-trichloroethyl)isonicotinamide compound of the formula:

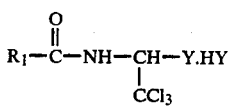 (IV)

wherein Y is halogen and $R_1$ is as defined above.
Then, a compound of the formula (IV) is reacted with a compound of the formula:

 (V)

wherein $R_2$ and X are as defined above, in an inorganic solvent preferably in the presence of a dehydrohalogenating agent at 0° to 150° C. for 30 min to 10 h to obtain a compound of the formula (I) of the present invention.

The inert solvents include aromatic hydrocarbons such as benzene, toluene and xylene; ethers such as diethyl ether, tetrahydrofuran and dioxane; halogenated hydrocarbons such as chloroform, 1,1,1-trichloroethane and carbon tetrachloride; ketones such as acetone and methyl isobutyl ketone; esters such as methyl acetate and ethyl acetate, acetonitrile; dimethyl sulfoxide; and dimethylformamide.

The dehydrohalogenating agents include inorganic bases such as sodium hydroxide, potassium hydroxide and potassium carbonate; and organic bases such as pyridine, triethylamine and N,N-diethylaniline.

In the compounds of the formula (I) of the present invention, examples of the $C_1$ to $C_{12}$ alkyls include ethyl, propyl, butyl, pentyl, hexyl, octyl, nonyl, decyl and lauryl; $C_3$ to $C_4$ alkenyls include allyl, and butenyl; $C_5$ or $C_6$ cycloalkyls include cyclopentyl and cyclohexyl; the $C_5$- or $C_6$-cycloalkyls substituted by $C_1$ or $C_2$-alkyl include 2-methylcyclopentyl and 2-methylcyclohexyl; the cyanoalkyl having 1 or 2 carbon atoms include cyanomethyl and cyanoethyl; the phenyl which may be substituted by one or more of $C_1$ to $C_4$-alkyl, $C_1$ to $C_4$-alkoxy, nitro, halogen, trifluoromethyl, allyl and methylcarbonyl include 3,4-dimethylphenyl, 2,5-dimethylphenyl, 2-methylphenyl, 4-ethylphenyl, 2-isopropylphenyl, 2-methoxyphenyl, 2-ethoxyphenyl, 3-isopropoxyphenyl, 4-chlorophenyl, 2-chlorophenyl, 3-chlorophenyl, 2,4-dichlorophenyl, 3,5-dichlorophenyl, 3,4-dichlorophenyl, 2-methyl-4-chlorophenyl, 3,4,5-trichlorophenyl, 2,4,6-trichlorophenyl, 2-fluorophenyl, 4-fluorophenyl, 3-trifluoromethylphenyl, 2-nitrophenyl, 2-chloro-4-nitrophenyl, 3-chloro-4-methoxyphenyl, 2-allylphenyl, 2-nitrophenyl, 4-iodophenyl, 4-methoxycarbonylphenyl and 3-methoxycarbonylphenyl; the benzyls substituted by methyl, chloro nitro, or methoxy include 4-chlorobenzyl, 4-methylbenzyl, 3-nitrobenzyl and 4-methoxybenzyl; the $C_1$ to $C_6$-alkyl substituted by halogen include —$CH_2CH_2Br$, —$CH_2CH_2Cl$, $CH_2CH_2CH_2Cl$, —$(CH_2)_5CH_2Br$, —$(CH_2)_5CH_2Cl$; and the $C_2$ or $C_3$-alkyls substituted by dimethylamino include —$(CH_2)_3N(CH_3)_2$ and —$CH_2CH_2N(CH_3)_2$.

Among the compounds of the formula (I) of the present invention, preferred ones, more preferred ones and particularly preferred ones in the following groups 1 to 3 will be mentioned below:

Group 1 (compounds of the formula (I) wherein X is oxygen):

Among them, preferred are those of the formula (I) wherein
X is oxygen,
$R_1$ is 3-pyridyl or 4-pyridyl, and
$R_2$ is $C_4$- to $C_6$-alkyl which may be substituted by halogen, benzyl or cycloalkyl.

More preferred compounds among those mentioned above are those of the formula (I) wherein:
X is oxygen,
$R_1$ is 3-pyridyl, and
$R_2$ is $C_4$- to $C_6$-alkyl or benzyl.

Particularly preferred compounds among those mentioned above are those of the formula (I) wherein:
X is oxygen,
$R_1$ is 3-pyridyl, and
$R_2$ is 3-methylbutyl, 3-methyl-2-butyl, 2-ethylbutyl, n-butyl or n-hexyl.

Group 2 (compounds of the formula (I) wherein X is sulfur):

Among them, preferred are those of the formula (I) wherein:
X is sulfur,
$R_1$ is 3-pyridyl or 4-pyridyl, and
$R_2$ is $C_4$- to $C_6$-alkyl or phenethyl.

More preferred compounds among those mentioned above are those of the formula (I) wherein:
X is sulfur,
$R_1$ is 3-pyridyl, and
$R_2$ is $C_4$- to $C_6$-alkyl.

Group 3

(compounds of the formula (I) wherein X is $-\underset{R_3}{N}-$):

Among them, preferred are those of the formula (I) wherein:
X is $-\underset{R_3}{N}-$, $R_1$ is 3-pyridyl or 4-pyridyl,
$R_2$ is $C_4$- to $C_6$-alkyl or benzyl, and
$R_3$ is hydrogen.

More preferred compounds among those mentioned above are those of the formula (I) wherein:
X is $-\underset{R_3}{N}-$, $R_1$ is 3-pyridyl,
$R_2$ is $C_4$- to $C_6$-alkyl, and
$R_3$ is hydrogen.

Particularly preferred compounds among those mentioned above are those of the formula (I) wherein:
X is $-\underset{R_3}{N}-$, $R_1$ is 3-pyridyl,
$R_2$ is 3-methylbutyl, 2-methylbutyl or n-hexyl, and
$R_3$ is hydrogen.

In the practical use of the compound of the formula (I) of the present invention as the agricultural and horticultural bactericide, it may be used after dilution with water or in the form of a dust, microgranules, granules, wettable powder, flowable agent, U.L.V. agent or emulsion prepared with an agricultural adjuvant by a method usually employed in the preparation of pesticides.

These preparations may be used either as such or after dilution with water to a suitable concentration.

The adjuvants used herein include carriers (liquid diluents and solids diluents), surfactants and organic materials.

The liquid diluents used as the carrier include aromatic hydrocarbons such as toluene, xylene and methylnaphthalene; alcohols such as isopropanol and glycol; esters such as butyl acetate; ketones such as cyclohexanone; amides such as dimethylformamide; sulfoxides such as dimethyl sulfoxide; cellosolves such as ethyl cellosolve; petroleum fractions such as kerosene; ethers such as dibutyl ether; chlorine-containing hydrocarbons such as chlorobenzene; animal and vegetable oils; fatty acids and esters of them; and water. The solid diluents used as the carrier include clay, kaolin, talc, diatomaceous earth, silica, calcium carbonate, montmorillonite, bentonite, feldspar, quartz and alumina.

The surfactants are those used as spreaders, emulsifying agents, wetting agents, dispersants and disintegrators. Examples of them include anionic, cationic, nonionic and amphoteric surfactants such as stearyltrimethylammonium chloride, sodium salt of higher alcohol sulfate, sodium ligninsulfonate, sodium naphthalenesulfonate/formalin condensate, ammonium salt of polyoxyethylene alkylbenzenesulfonate, sodium alkylbenzenesulfonates, polyoxyethylene alkylphenyl ethers, polyoxyethylene alkyl ethers and laurylbetaine.

The organic materials are those used as fixing agent, binders, disintegrators, stabilizers, fluidizing agents and thickening agents. Examples of them include carboxymethylcellulose, polyvinyl alcohol, polyethylene glycol, sodium polyacrylate, acacia, isopropylamide phosphate and xanthane gum.

These preparations may be used either alone or in the form of a mixture with a herbicide, insecticide, plant growth regulator, acaricide or fungicide.

The amount of the compound used as the active ingredient of the agricultural and horticultural bactericide of the present invention varies depending on the type of the preparation, application method and other conditions. Though the active component may be used alone, it is used usually in an amount of 0.5 to 95 wt. % in combination with other components.

The preferred amount of the active ingredient varies depending on the type of the preparation. For example, the dust comprises 0.5 to 20% (by weight; the same shall apply hereinafter) of the active ingredient and 80 to 99.5% of the adjuvant; the emulsion comprises 5 to 80% of the active ingredient and 20 to 95% of the adjuvant, the flowable composition comprises 5 to 70% of the active ingredient and 30 to 95% of the adjuvant, the wettable powder comprises 5 to 90% of the active ingredient and 10 to 95% of the adjuvant, the granules and the microgranules comprise 0.5 to 15% of the active ingredient and 85 to 99.5% of the adjuvant.

The compounds of the present invention are used as agricultural and horticultural bactericides which exhibit an excellent effect of controlling bacterial leaf blight of rice without exhibiting phytotoxicity to crops when the soil of a paddy field is treated with them or when they are sprayed onto the stems and leafs of rice plant. In addition, they are effective also in controlling citrus canker and soft rot of Chinese cabbages.

The following examples will further illustrate the present invention.

SYNTHESIS EXAMPLES

Synthesis Example 1

Synthesis of Compound No. 1 of the present invention 150 ml of benzene was added to 10.0 g of N-(1-hydroxy-2,2,2-trichloroethyl)nicotinamide. 5.3 g of thionyl chloride was added dropwise thereto and the mixture was heated under reflux (60° to 80° C.) for about 5 h under stirring to complete the production of N-(1,2,2,2-tetrachloroethyl)nicotinamide. The reaction liquid was cooled to 30° C. or below. 20 ml of methanol was added to the liquid. 4.0 g of triethylamine was added dropwise to the liquid mixture while it was kept at 5° C. and the obtained mixture was stirred at room temperature for 3 h. Then, the mixture was kept at room temperature overnight. The reaction liquid was poured in an aqueous sodium bicarbonate solution and a benzene layer thus separated was washed with saturated aqueous common salt solution and water and dried over anhydrous sodium sulfate. After concentration, the residue was recrystallized from methanol to obtain 4.8 g of N-(1-methoxy-2,2,2-trichloroethyl)nicotinamide.

m.p. 151° to 152° C.

Synthesis Example 2

Synthesis of Compound No. 23 of the present invention 2.7 g of triethylamine was added dropwise to a liquid mixture of 7.0 g of N-(1,2,2,2-tetrachloroethyl)isonicotinamide, 60 ml of acetonitrile and 4.4 g of 2,4-dichlorophenol at a temperature of up to 5° C. After stirring at room temperature for 2 h, the reaction liquid was heated and the reaction was carried out at 50° to 60° C. for 3 h. The reaction mixture was cooled to room temperature and poured in water to precipitate crystals. The crystals were filtered, washed with water, dried and recrystallized from a solvent mixture of n-hexane and ethyl acetate to obtain 5.6 g of N-[1-(2',4'-dichlorophenoxy)-2,2,2-trichloroethyl]isonicotinamide.

m.p. 158° to 160° C.

The compounds of the present invention which can be synthesized in the same manner as in Synthesis Example 1 or 2 are shown in Table 1.

TABLE 1

$$R_1-\overset{O}{\underset{}{C}}-NH-\underset{CCl_3}{\underset{|}{CH}}-O-R_4$$

| Compound No. | $R_1$ | $R_4$ | Melting point or refractive index |
|---|---|---|---|
| 1 | 3-pyridyl | —CH$_3$ | m.p. 151–152° C. |
| 2 | " | —C$_2$H$_5$ | m.p. 87–88° C. |
| 3 | " | —C$_3$H$_7$ (iso) | m.p. 132–133° C. |
| 4 | " | —C$_4$H$_9$ (n) | $n_D^{25}$ 1.5360 |
| 5 | " | —CH$_2$CH=CH$_2$ | m.p. 78–79° C. |
| 6 | " | —CH$_2$CH$_2$—O—CH$_3$ | m.p. 99–102° C. |
| 7 | " | —CH$_2$CH$_2$Cl | m.p. 92–94° C. |
| 8 | " | —CH$_2$CH$_2$Br | m.p. 108–111° C. |
| 9 | " | —phenyl | m.p. 177–178° C. |
| 10 | " | —(2-chlorophenyl) | m.p. 137–139° C. |

TABLE 1-continued $$R_1-\overset{\overset{O}{\|}}{C}-NH-\underset{\underset{CCl_3}{|}}{CH}-O-R_4$$

| Compound No. | R₁ | R₄ | Melting point or refractive index |
|---|---|---|---|
| 11 | " | 2,4-dichlorophenyl | m.p. 118–120° C. |
| 12 | " | 3-nitrophenyl | m.p. 121–124° C. |
| 13 | " | 2-methylphenyl | m.p. 122–124° C. |
| 14 | " | cyclohexyl | m.p. 171–173° C. |
| 15 | " | 2-methoxyphenyl | m.p. 126–128° C. |
| 16 | " | 2-allylphenyl (—CH₂CH=CH₂ substituted phenyl) | m.p. 115–117° C. |
| 17 | " | —CH₂-phenyl | m.p. 119–121° C. |
| 18 | " | —CH₂-(2-chlorophenyl) | m.p. 94–96° C. |
| 19 | " | 2-ethylcyclohexyl | $n_D^{25}$ 1.5415 |
| 20 | 4-pyridyl | —C₄H₉ (n) | m.p. 78–80° C. |
| 21 | " | —CH₂CH₂CH₂Cl | m.p. 82–85° C. |

TABLE 1-continued
$$R_1-\overset{O}{\overset{\|}{C}}-NH-\underset{\underset{CCl_3}{|}}{CH}-O-R_4$$
| Compound No. | R₁ | R₄ | Melting point or refractive index |
|---|---|---|---|
| 22 | " |  | m.p. 137–139° C. |
| 23 | " | 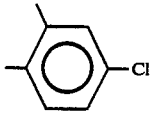 | m.p. 158–160° C. |
| 24 | 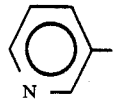 | —C₆H₁₃ (n) | $n_D^{25}$ 1.5205 |
| 25 | " | —(CH₂)₄Cl | $n_D^{25}$ 1.5354 |
| 26 | " | —(CH₂)₅CH₂Cl | $n_D^{25}$ 1.5348 |
| 27 | " | 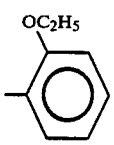 | m.p. 117–118° C. |
| 28 | " | 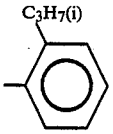 | m.p. 120–122° C. |
| 29 | " | 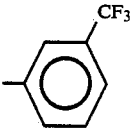 | m.p. 148–150° C. |
| 30 | " | 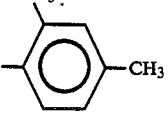 | m.p. 194–196° C. |
| 31 | " | 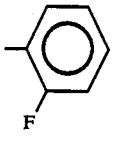 | m.p. 135–138° C. |
| 32 | " | 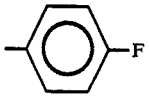 | m.p. 147–149° C. |
| 33 | " | 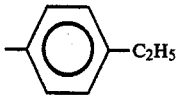 | m.p. 1.5376 |

TABLE 1-continued $$R_1-\overset{\overset{O}{\|}}{C}-NH-\underset{\underset{CCl_3}{|}}{CH}-O-R_4$$

| Compound No. | R₁ | R₄ | Melting point or refractive index |
|---|---|---|---|
| 34 | " | —CH₂—⟨C₆H₄⟩—Cl | m.p. 112–113° C. |
| 35 | " | 2,4,5-trichlorophenyl | m.p. 136–139° C. |
| 36 | " | —C₃H₇ (n) | m.p. 79–81° C. |
| 37 | " | —C₄H₉ (iso) | m.p. 95–97° C. |
| 38 | " | —C₄H₉ (sec) | m.p. 83–85° C. |
| 39 | " | —C₄H₉ (tert) | m.p. 162–164° C. |
| 40 | " | —CH₂CH═CH.CH₃ | m.p. 75–77° C. |
| 41 | " | —C₅H₁₁ (n) | $n_D^{25}$ 1.5280 |
| 42 | " | —C₅H₁₁ (iso) | m.p. 62–64° C. |
| 43 | " | —CH(CH₃)—CH₂CH₂CH₃ | m.p. 78–80° C. |
| 44 | " | —CH(CH₃)—CH(CH₃)₂ | m.p. 78–80° C. |
| 45 | " | —CH₂CH(C₂H₅)₂ | $n_D^{25}$ 1.5285 |
| 46 | " | —C₈H₁₇ (n) | $n_D^{25}$ 1.5186 |
| 47 | " | 3-chlorophenyl | m.p. 147–149° C. |
| 48 | " | 2,4-dichlorophenyl | m.p. 120–122° C. |
| 49 | " | 2,4-dichlorophenyl | m.p. 191–193° C. |
| 50 | " | —CH(CH₃)—⟨C₆H₅⟩ | m.p. 115–117° C. |
| 51 | " | tetrahydrofuryl (H) | m.p. 154–156° C. |

Synthesis Example 3

Synthesis of Compound No. 57 of the present invention 150 ml of benzene was added to 5.0 g of N-(1-hydroxy-2,2,2-trichloroethyl)nicotinamide. 2.6 g of thionyl chloride was added dropwise to the mixture under stirring. Then, the mixture was heated under reflux (60° to 80° C.) for about 5 h to complete the production of N-(1,2,2,2-tetrachloroethyl)nicotinamide. The reaction liquid was cooled to 30° C. or below and 1.7 g of sec-butylmercaptan was added thereto. 3.7 g of triethylamine was added dropwise to the liquid mixture while it was kept at 5° C. The obtained mixture was stirred at room temperature for 3 h and then left to stand at room temperature overnight. The reaction liquid was poured in an aqueous sodium bicarbonate solution and a benzene layer thus separated was washed with a saturated aqueous common salt solution and water and then dried over anhydrous sodium sulfate. After concentration, the residue was recrystallized from a solvent mixture of n-hexane and ethyl acetate to obtain 2.5 g of N-(1-sec-butylthio-2,2,2-trichloroethyl)nicotinamide.

m.p. 70° to 72° C.

Synthesis Example 4

Synthesis of Compound No. 83 of the present invention:

3.7 g of triethylamine was added dropwise to a liquid mixture of 6.0 g of N-(1,2,2,2-tetrachloroethyl)isonicotinamide, 150 ml of acetonitrile and 2.9 g of 4-chlorobenzylmercaptan at a temperature of up to 5° C. The mixture was stirred at room temperature for 2 h and then heated to 50° to 60° C. to carry out the reaction for 3 h. The reaction mixture was cooled to room temperature and poured in water to precipitate crystals. The crystals were filtered, washed with water, dried and recrystallized from a solvent mixture of n-hexane and ethyl acetate to obtain 3.6 g of N-[1-(4'-chlorobenzylethio)-2,2,2-trichloroethyl]isonicotinamide.

m.p. 53° to 56° C.

The compounds of the present invention which can be synthesized in the same manner as in Synthesis Example 3 or 4 are shown in Table 2.

TABLE 2

General formula:

$$R_1-\overset{O}{\underset{}{C}}-NH-\underset{CCl_3}{\overset{}{CH}}-S-R_5$$

| Compound No. | $R_1$ | $R_5$ | Melting point or refractive index |
|---|---|---|---|
| 52 | 3-pyridyl | $-C_2H_5$ | m.p. 105–107° C. |
| 53 | " | $-C_3H_7$ (n) | m.p. 110–112° C. |
| 54 | " | $-C_3H_7$ (iso) | m.p. 118–120° C. |
| 55 | " | $-CH_2CH=CH_2$ | m.p. 127–129° C. |
| 56 | " | $-C_4H_9$ (n) | m.p. 100–101° C. |
| 57 | " | $-C_4H_9$ (sec) | m.p. 70–72° C. |
| 58 | " | $-C_4H_9$ (iso) | m.p. 103–105° C. |
| 59 | " | $-C_5H_{11}$ (sec) | $n_D^{25}$ 1.5630 |
| 60 | " | $-C_6H_{13}$ (n) | m.p. 66–68° C. |
| 61 | " | $-C_8H_{17}$ (n) | m.p. 54–56° C. |
| 62 | " | $-C_{12}H_{25}$ (n) | m.p. 61–63° C. |
| 63 | " | phenyl | m.p. 147–149° C. |
| 64 | " | 4-Cl-phenyl | m.p. 160–161° C. |
| 65 | " | 2,4,6-trichlorophenyl | m.p. 134–135° C. |
| 66 | " | 4-$NO_2$-phenyl | m.p. 176–178° C. |
| 67 | " | 2-$CH_3$-phenyl | m.p. 95–97° C. |
| 68 | " | $-CH_2$-phenyl | m.p. 116–118° C. |

TABLE 2-continued

General formula:

$$R_1-\overset{\overset{O}{\|}}{C}-NH-\underset{\underset{CCl_3}{|}}{CH}-S-R_5$$

| Compound No. | R₁ | R₅ | Melting point or refractive index |
|---|---|---|---|
| 69 | " | —CH₂—C₆H₄—Cl | m.p. 133–135° C. |
| 70 | " | —CH₂—C₆H₄—CH₃ | m.p. 122–124° C. |
| 71 | " | —CH₂—C₆H₄—OCH₃ | m.p. 94–96° C. |
| 72 | " | —CH₂—CH₂—C₆H₅ | m.p. 99–100° C. |
| 73 | " | cyclopentyl | m.p. 135–137° C. |
| 74 | " | cyclohexyl | m.p. 111–113° C. |
| 75 | " | 2-pyridyl | m.p. 75–78° C. |
| 76 | " | —CH₂-(2-pyridyl) | m.p. 137–139° C. |
| 77 | 4-pyridyl | —C₃H₇ (iso) | m.p. 145–147° C. |
| 78 | " | —CH₂CH=CH₂ | m.p. 46–50° C. |
| 79 | " | —C₄H₉ (n) | m.p. 97–99° C. |
| 80 | " | —C₄H₉ (tert) | m.p. 176–178° C. |
| 81 | " | —C₅H₁₁ (n) | m.p. 80–82° C. |
| 82 | " | —C₆H₄—Cl | m.p. 136–138° C. |
| 83 | " | —CH₂—C₆H₄—Cl | m.p. 53–56° C. |

TABLE 2-continued

General formula:

$$R_1-\overset{O}{\overset{\|}{C}}-NH-\underset{\underset{CCl_3}{|}}{CH}-S-R_5$$

| Compound No. | $R_1$ | $R_5$ | Melting point or refractive index |
|---|---|---|---|
| 84 | " | —CH$_2$—(phenyl with NO$_2$) | |
| 85 | " | —(phenyl with Cl and OCH$_3$) | |

Synthesis Example 5

Synthesis of Compound No. 88 of the present invention 150 ml of benzene was added to 5.0 g of N-(1-hydroxy-2,2,2-trichloroethyl)nicotinamide. 2.6 g of thionyl chloride was added dropwise to the mixture under stirring and the obtained mixture was heated under stirring at 60° to 80° C. for about 5 h to complete the production of N-(1,2,2,2-tetrachloroethyl)nicotinamide. The reaction solution was cooled to a temperature of 30° C. or below. 1.4 g of 2-methoxyethylamine was added thereto and then 3.7 g of triethylamine was added dropwise to the liquid mixture kept at 5° C. After stirring at room temperature for 3 h, the mixture was left to stand at room temperature overnight. The reaction solution was poured in an aqueous sodium bicarbonate solution. A benzene layer thus separated was washed with a saturated aqueous common salt solution and water and dried over anhydrous sodium sulfate. After concentration, the residue was recrystallized from a solvent mixture of n-hexane and ethyl acetate to obtain 2.5 g of N-(2-methoxyethylamino-2,2,2-trichloroethyl)-nicotinamide. m.p. 75° to 77° C.

Synthesis Example 6

Synthesis of Compound No. 130 of the present invention 3.7 g of triethylamine was added dropwise to a liquid mixture of 6.0 g of N-(1,2,2,2-tetrachloroethyl)isonicotinamide. 100 ml of acetonitrile and 2.2 g of phenethylamine at a temperature of up to 5° C. The mixture was stirred at room temperature for 2 h and the obtained reaction solution was heated to 50° to 60° C. to carry out the reaction for 3 h, cooled to room temperature and poured in water to precipitate crystals. The crystals were filtered, washed with water, dried and recrystallized from a solvent mixture of n-hexane and ethyl acetate to obtain 3.2 g of N-[1-(phenethylamino)-2,2,2-trichloroethyl]isonicotinamide. m.p. 115° to 117° C.

The compounds of the present invention which can be synthesized in the same manner as in Synthesis Example 5 or 6 are shown in Table 3.

TABLE 3

Formula:

$$R_1-\overset{O}{\overset{\|}{C}}-NH-\underset{\underset{CCl_3}{|}}{CH}-N\overset{R_7}{\underset{R_8}{\diagdown}}$$

| Compound No. | $R_1$ | $R_7$ | $R_8$ | Melting point or refractive index |
|---|---|---|---|---|
| 86 | (pyridyl) | —H | —C$_3$H$_7$(iso) | m.p. 110–112° C. |
| 87 | " | " | —CH$_2$—CH=CH$_2$ | m.p. 134–136° C. |
| 88 | " | " | —CH$_2$CH$_2$—O—CH$_3$ | m.p. 75–77° C. |
| 89 | " | " | —C$_4$H$_9$(n) | m.p. 89–91° C. |
| 90 | " | " | —C$_4$H$_9$(iso) | m.p. 130–132° C. |
| 91 | " | " | —C$_4$H$_9$(sec) | m.p. 43–46° C. |
| 92 | " | " | —C$_5$H$_{11}$(n) | m.p. 73–75° C. |
| 93 | " | " | —C$_5$H$_{11}$(iso) | m.p. 110–112° C. |
| 94 | " | " | —CH$_2$—CH(CH$_3$)—C$_2$H$_5$ | m.p. 107–109° C. |

TABLE 3-continued

Formula:

$$R_1-\overset{\overset{O}{\|}}{C}-NH-\underset{\underset{CCl_3}{|}}{CH}-N\overset{R_7}{\underset{R_8}{\diagdown}}$$

| Compound No. | $R_1$ | $R_7$ | $R_8$ | Melting point or refractive index |
|---|---|---|---|---|
| 95 | " | " | —$C_6H_{13}$(n) | m.p. 78–80° C. |
| 96 | " | " | —$C_8H_{17}$(n) | m.p. 64–67° C. |
| 97 | " | " | —$(CH_2)_3N(CH_3)_2$ | $n_D^{25}$ 1.5420 |
| 98 | " | " | phenyl | m.p. 207–209° C. |
| 99 | " | " | 2-Cl-phenyl | m.p. 145–147° C. |
| 100 | " | " | 3-Cl-phenyl | m.p. 197–199° C. |
| 101 | " | " | 4-Cl-phenyl | m.p. 179–180° C. |
| 102 | " | " | 2,4-diCl-phenyl | m.p. 94–97° C. |
| 103 | " | " | 3,5-diCl-phenyl | m.p. 200–202° C. |
| 104 | " | " | 3,4-diCl-phenyl | m.p. 196–198° C. |
| 105 | " | " | 2-CH$_3$-4-Cl-phenyl | m.p. 176–178° C. |
| 106 | " | " | 2-Cl-4-NO$_2$-phenyl | m.p. 75–79° C. |

TABLE 3-continued

Formula:

$$R_1-\overset{O}{\underset{\|}{C}}-NH-\underset{\underset{CCl_3}{|}}{CH}-N\overset{R_7}{\underset{R_8}{\diagdown}}$$

| Compound No. | R$_1$ | R$_7$ | R$_8$ | Melting point or refractive index |
|---|---|---|---|---|
| 107 | " | " | 2,4,6-trichlorophenyl | m.p. 145–147° C. |
| 108 | " | " | 4-fluorophenyl | m.p. 178–180° C. |
| 109 | " | " | 2-fluorophenyl | m.p. 161–163° C. |
| 110 | " | " | 3-trifluoromethylphenyl | m.p. 90–91° C. |
| 111 | " | " | 2-nitrophenyl | m.p. 94–98° C. |
| 112 | " | " | 2-ethylphenyl | m.p. 168–170° C. |
| 113 | " | " | 2,4-dimethylphenyl | m.p. 140–141° C. |
| 114 | " | " | 2-methoxyphenyl | m.p. 166–167° C. |
| 115 | " | " | 3-isopropoxyphenyl | m.p. 90–92° C. |
| 116 | " | " | —CH$_2$—phenyl | m.p. 133–135° C. |

TABLE 3-continued

Formula:

$$R_1-\underset{\underset{}{\overset{O}{\|}}}{C}-NH-\underset{\underset{CCl_3}{|}}{CH}-N\underset{R_8}{\overset{R_7}{\diagdown}}$$

| Compound No. | $R_1$ | $R_7$ | $R_8$ | Melting point or refractive index |
|---|---|---|---|---|
| 117 | " | " | —CH₂—⟨C₆H₄⟩—Cl | m.p. 169–171° C. |
| 118 | " | " | —⟨C₆H₁₁⟩ | m.p. 157–159° C. |
| 119 | " | " | —⟨C₆H₁₀⟩—CH₃ | m.p. 110–113° C. |
| 120 | " | " | —CH₂—⟨thiophene⟩ | m.p. 127–129° C. |
| 121 | " | " | —CH₂—⟨pyridyl⟩ | m.p. 131–133° C. |
| 122 | ⟨4-pyridyl⟩— | " | —CH₂CH₂—Cl | $n_D^{25}$ 1.5560 |
| 123 | " | " | —C₄H₉(n) | m.p. 119–121° C. |
| 124 | " | H | —C₄H₉(sec) | m.p. 116–118° C. |
| 125 | " | " | —CH₂—CH(C₂H₅)—(CH₂)₃CH₃ | $n_D^{25}$ 1.5240 |
| 126 | " | " | —C₁₂H₂₅(n) | $n_D^{25}$ 1.5125 |
| 127 | " | " | —⟨C₆H₄⟩—I | m.p. 190–193° C. |
| 128 | " | " | —⟨C₆H₃⟩(Cl)(Cl) | m.p. 146–148° C. |
| 129 | " | " | —⟨C₆H₄⟩—C(=O)—OCH₃ | m.p. 182–184° C. |
| 130 | " | " | —CH₂CH₂—⟨C₆H₅⟩ | m.p. 115–117° C. |

TABLE 3-continued

Formula:

$$R_1-\overset{O}{\underset{\parallel}{C}}-NH-\underset{\underset{CCl_3}{|}}{CH}-N\overset{R_7}{\underset{R_8}{\diagdown}}$$

| Compound No. | $R_1$ | $R_7$ | $R_8$ | Melting point or refractive index |
|---|---|---|---|---|
| 131 | " | " | —CH$_2$—(furan) | m.p. 117–119° C. |
| 132 | " | —CH$_2$CN | —CH$_2$CN | m.p. 195–198° C. |
| 133 | (pyridyl) | —C$_2$H$_5$ | —C$_2$H$_5$ | m.p. 60–63° C. |
| 134 | " | —C$_3$H$_7$(n) | —C$_2$H$_5$ | m.p. 48–50° C. |
| 135 | " | —H | —CH(C$_2$H$_5$)—CH$_2$—OCH$_3$ | m.p. 65–68° C. |
| 136 | " | —C$_4$H$_9$(n) | —CH$_3$ | m.p. 47–49° C. |
| 137 | " | " | —C$_4$H$_9$(n) | m.p. 108–110° C. |
| 138 | " | " | —(phenyl) | m.p. 93–95° C. |
| 139 | " | —CH(CH$_3$)—C(O)—OC$_3$H$_7$(iso) | —CH$_2$—(furan) | $n_D^{25}$ 1.5420 |
| 140 | " | —H | —CH$_2$COOCH$_3$ | |
| 141 | " | H | —(cyclopentyl-H) | |
| 142 | " | H | —CH(CH$_3$)—(phenyl) | m.p. 137–139° C. |

FORMULATION EXAMPLES

Formulation Example 1

Wettable powder 20 parts of Compound No. 10 of the present invention, i.e. N-[1-(2'-chlorophenoxy)-2,2,2-trichloroethyl]-nicotinamide, 75 parts of kaolin, 3 parts of sodium salt of higher alcohol sulfate and 2 parts of sodium polyacrylate were mixed together and pulverized to obtain a wettable powder.

Formulation Example 2

Emulsion 30 parts of Compound No. 4 of the present invention, i.e. N-(1-n-butoxy-2,2,2-trichloroethyl)nicotinamide, was dissolved in 53 parts of xylene. The solution was mixed with a mixture of an alkylphenol-ethylene oxide condensate and a calcium alkylbenzenesulfonate (8:2) to obtain an emulsion.

This emulsion is to be diluted with water to obtain a diluted emulsion when it is used.

Formulation Example 3

Dust 1 part of Compound No. 7 of the present invention, i.e. N-[1-(2'-chloroethoxy-2,2,2-trichloroethyl]nicotinamide, was mixed with 49 parts of talc and 50 parts of clay and the mixture was pulverized to obtain a dust.

Formulation Example 4

Microgranules

5 Parts of Compound No. 22 of the present invention, i.e. N-(1-phenoxy-2,2,2-trichloroethyl)isonicotinamide, 6 parts of bentonite and 9 parts of clay were mixed together homogeneously and pulverized to obtain a dense dust. Separately, 80 parts of a coarse powder of a mineral material having a particle size of 74 to 105μ and oil-nonabsorptivity was introduced into a suitable mixer and 20 parts of water was added thereto under rotation of the mixer to uniformly wet the powder. The dense dust was added thereto to effect the coating. After drying, microgranules were obtained.

Formulation Example 5

Granules 10 parts of compound No. 20, i.e. N-(1-n-butoxy-2,2,2-trichloroethyl)isocinotinamide, 35 parts of diatomaceous earth, 23 parts of bentonite, 30 parts of talc and 2 parts of a disintegrator were mixed together. 18 parts of water was added to the mixture to wet it uniformly. The mixture was extruded by means of an injection molding machine to form granules. The granules were treated in a disintegrator and then an adjuster to dress and to obtain the granules having a diameter of 0.6 to 1 mm.

EXPERIMENTAL EXAMPLES

Experimental Example 1

Test of controlling bacterial leaf blight of rice with submerged application

A rice plant (variety: Musashi-kogane) was raised in plastic pots having a size of 15 cm×5 cm×10 cm (height) for 1.5 months. Granules prepared from the compound of the present invention shown in Table 2 were applied to the soil in the pot in a given amount. After three days, leaves of the rice plant were inoculated with *Xanthomonas campestris p.v. oryzae* by clip inoculation with scissors. After keeping them in a greenhouse at 30° C. for 24 h to effect the infection, the disease was further developed in the greenhouse.

The same procedure as above was repeated using 8% Probenazol granules (active ingredient: 1,2-benzisothiazol-3-one 1,1-dioxide) as a standard chemical.

The length of the disease symptoms of leaf were measured 21 days after the inoculation.

The results are shown in Table 4.

TABLE 4

| Tested compound | Amount of active ingredient | Average spot length | Phytotoxicity |
|---|---|---|---|
| Compound No. of the present invention | | | |
| 1 | 10 mg/pot | 4.0 cm | none |
| 2 | " | 3.8 | " |
| 3 | " | 3.7 | " |
| 4 | " | 0.2 | " |
| 7 | " | 3.0 | " |
| 8 | " | 0.3 | " |
| 9 | " | 3.4 | " |
| 10 | " | 2.9 | " |
| 11 | " | 1.1 | " |
| 20 | " | 0.5 cm | " |
| 21 | " | 0.3 | " |
| 22 | " | 3.1 | " |
| 23 | " | 3.5 | " |
| 36 | " | 0.8 | " |
| 37 | " | 0.9 | " |
| 38 | " | 0.3 | " |
| 39 | " | 3.9 | " |
| 40 | " | 1.0 | " |
| 41 | " | 0.8 | " |
| 42 | " | 0.7 | " |
| 43 | " | 0.6 | " |
| 44 | " | 0.9 | " |
| 45 | " | 1.0 | " |
| 46 | " | 3.8 | " |
| 47 | " | 3.7 | " |

TABLE 4-continued

| Tested compound | Amount of active ingredient | Average spot length | Phytotoxicity |
|---|---|---|---|
| 48 | " | 2.8 | " |
| 49 | " | 3.4 | " |
| 50 | " | 1.2 | " |
| 51 | " | 1.3 | " |
| 52 | " | 3.8 | " |
| 53 | " | 2.8 | " |
| 55 | " | 2.1 | " |
| 56 | " | 0.3 cm | " |
| 57 | " | 0.5 | " |
| 58 | " | 1.2 | " |
| 59 | " | 0.9 | " |
| 61 | " | 2.9 | " |
| 65 | " | 3.3 | " |
| 66 | " | 2.8 | " |
| 67 | " | 3.1 | " |
| 68 | " | 1.5 | " |
| 69 | " | 3.2 | " |
| 70 | " | 4.2 | " |
| 71 | " | 2.4 | " |
| 72 | " | 1.7 | " |
| 73 | " | 1.6 | " |
| 74 | " | 2.0 | " |
| 75 | " | 3.5 | " |
| 76 | " | 3.0 | " |
| 87 | " | 2.0 | " |
| 88 | " | 0.5 | " |
| 89 | " | 0.4 | " |
| 90 | " | 0.9 | " |
| 95 | " | 0.6 | " |
| 96 | " | 1.7 | " |
| 98 | " | 4.0 cm | " |
| 104 | " | 3.7 | " |
| 107 | " | 2.8 | " |
| 109 | " | 1.0 | " |
| 110 | " | 2.5 | " |
| 114 | " | 0.5 | " |
| 115 | " | 1.5 | " |
| 116 | " | 1.3 | " |
| 118 | " | 2.7 | " |
| 120 | " | 1.8 | " |
| 121 | " | 1.2 | " |
| 138 | " | 3.0 | " |
| 139 | " | 3.5 | " |
| 142 | " | 3.2 | " |
| Control | | | |
| Probenazol | 40 mg/pot | 4.4 | yellowing |
| Untreated | | 11.6 | none |

Experimental Example 2

Tests of controlling bacterial leaf blight of rice with foliar spray

A rice plant (variety: Musashi-kogane) was raised in plastic pots having a size of 15 cm×5 cm×10 cm (height) for 1.5 months. A given amount of a wettable powder prepared from the compound of the present invention shown in Table 3 was sprayed on the rice plant. After one day, the leaves of the rice plant were infected with *Xanthomonas campestris p.v. oryzae* with pin prick inoculation. After keeping them in a greenhouse at 30° C. for 24 h to effect the infection, the disease was further developed in the greenhouse.

For control, the same procedure as above was repeated using 10% phenazine wettable powder (active ingredient: phenazine-5-oxide) as a standard chemical.

21 days after the inoculation, the rate of diseased leaves [(number of diseased leaves)/(number of total leaves)×100] was determined.

The results are shown in Table 5.

TABLE 5

| Tested compound | Concentration | Rate of diseased leaves (%) | Phytotoxicity |
|---|---|---|---|
| Compound No. of the present invention | | | |
| 1 | 200 ppm | 40 | none |
| 2 | " | 37 | none |
| 3 | " | 41 | none |
| 4 | " | 12 | none |
| 7 | " | 37 | none |
| 8 | " | 28 | none |
| 9 | " | 48 | none |
| 10 | " | 30 | none |
| 11 | " | 16 | none |
| 20 | " | 60 | none |
| 21 | " | 17 | none |
| 22 | " | 29 | none |
| 23 | " | 63 | none |
| 36 | " | 59 | none |
| 37 | " | 38 | none |
| 38 | " | 21 | none |
| 39 | " | 68 | none |
| 40 | " | 19 | none |
| 41 | " | 15 | none |
| 42 | " | 9 | none |
| 43 | " | 8 | none |
| 44 | " | 10 | none |
| 45 | " | 10 | none |
| 46 | " | 42 | none |
| 47 | " | 37 | none |
| 48 | " | 35 | none |
| 49 | " | 53 | none |
| 50 | " | 14 | none |
| 51 | " | 30 | none |
| 52 | " | 39 | none |
| 54 | " | 51 | none |
| 56 | " | 15 | none |
| 58 | " | 36 | none |
| 60 | " | 29 | none |
| 62 | " | 40 | none |
| 63 | " | 42 | none |
| 64 | " | 44 | none |
| 65 | " | 49 | none |
| 66 | " | 35 | none |
| 67 | " | 41 | none |
| 68 | " | 52 | none |
| 69 | " | 39 | none |
| 70 | " | 36 | none |
| 71 | " | 20 | none |
| 72 | " | 16 | none |
| 73 | " | 42 | none |
| 74 | " | 15 | none |
| 75 | " | 33 | none |
| 76 | " | 49 | none |
| 86 | " | 36 | none |
| 88 | " | 28 | none |
| 89 | " | 20 | none |
| 90 | " | 14 | none |
| 95 | " | 11 | none |
| 96 | " | 23 | none |
| 100 | " | 42 | none |
| 102 | " | 24 | none |
| 103 | " | 38 | none |
| 104 | " | 21 | none |
| 107 | " | 34 | none |
| 108 | " | 51 | none |
| 110 | " | 25 | none |
| 112 | " | 35 | none |
| 114 | " | 19 | none |
| 116 | " | 12 | none |
| 119 | " | 25 | none |
| 120 | " | 24 | none |
| 121 | " | 24 | none |
| 135 | " | 60 | none |
| 138 | " | 45 | none |
| 139 | " | 58 | none |
| 142 | " | 44 | none |
| Control | | | |
| Phenazine | 200 ppm | 74 | none |
| untreated | — | 100 | — |

Experimental Example 3

Antifungal activity tests 20 ml of a potato/agar culture medium was poured in each of Petri dishes having a diameter of 9 cm. The compound of the present invention was mixed therein to obtain a given concentration. *Xanthomonas campestris p.v. citri* and *Ervinia aroideae* were applied thereto. After the culture conducted at 25° C. for 3 day, the growth of the fungi was examined.

The results are shown in terms of the minimum growth inhibitory concentration in Table 6.

TABLE 6

| Tested No. compound | Minimum growth inhibitory conc. (ppm) | |
|---|---|---|
| | *Xanthomonas campestris p.v. citri* | *Erwinia aroideae* |
| 4 | | 100 |
| 7 | | 500 |
| 8 | | 500 |
| 9 | | 500 |
| 10 | | 500 |
| 11 | 500 | 500 |
| 20 | | 500 |
| 21 | | 100 |
| 22 | | 500 |
| 23 | 500 | 500 |
| 86 | — | 500 |
| 89 | — | 500 |
| 90 | — | 500 |
| 99 | — | 500 |
| 102 | 500 | 20 |
| 106 | — | 100 |
| 110 | — | 500 |
| 113 | — | 500 |
| 127 | — | 500 |
| 128 | — | 500 |
| 137 | — | 500 |

Experimental Example 4

Tests of controlling black rot of cabbages with foliar spray

A given amount of a wettable powder of the present invention prepared according to the method shown in Formulation Example 1 was sprayed on cabbages (tri- to tetrafoliate stage) (variety: Shogun) raised in pots having a diameter of 10 cm. Then, the cabbage leaves were inoculated with *Xanthomonas campestries p.v. campestris* by a clip inoculation with scissors. They were kept in a greenhouse at 30° C. to develop the disease.

The same procedure as above was repeated using 10% wettable powder of streptomycin as a standard chemical.

14 days after the inoculation, the lengths of the spots were examined.

The results are shown in Table 7.

TABLE 7

| Tested compound | Conc. (ppm) | Average spot length (cm) | Phytotoxicity |
|---|---|---|---|
| Compound No. of the present invention | | | |
| 4 | 500 | 1.2 | none |
| 10 | " | 1.8 | none |
| 20 | " | 2.0 | none |
| 56 | " | 2.5 | none |
| 57 | " | 2.2 | none |
| 58 | " | 1.6 | none |
| 59 | " | 1.8 | none |
| 60 | " | 2.5 | none |
| 89 | " | 1.9 | none |

TABLE 7-continued

| Tested compound | Conc. (ppm) | Average spot length (cm) | Phytotoxicity |
|---|---|---|---|
| 90 | " | 1.4 | none |
| 91 | " | 1.6 | none |
| 92 | " | 2.0 | none |
| 93 | " | 2.4 | none |
| 94 | " | 2.0 | none |
| Control |  |  |  |
| Streptomycin | 200 | 4.8 | none |
| Untreated | — | 4.8 | — |

What we claim is:

1. A compound of the formula:

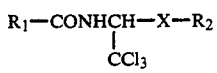 (1)

wherein

X is oxygen, sulfur or

$R_1$ is 3-pyridyl or 4-pyridyl, $R_2$ is $C_1 \sim C_{12}$-alkyl; $C_3$ or $C_4$-alkenyl; $C_5$- or $C_6$-cycloalkyl which may be substituted by $C_1$- or $C_2$-alkyl; pyridyl; pyridylmethyl; phenethyl; cyano alkyl having one or two carbon atoms; methoxymethyl; methoxymethylpropyl; phenyl; phenyl which is substituted by one or more of $C_1 \sim C_4$-alkyl, $C_1 \sim C_4$-alkoxy, nitro, halogen, trifluoromethyl, allyl and methoxycarbonyl; benzyl; benzyl which is substituted by one or more of methyl, nitro, methoxy and chloro; α-methylbenzyl; $C_1 \sim C_6$-alkyl which is substituted by halogen when X is oxygen or

—N—;
|
$R_3$ $C_2$- or $C_3$-alkyl which is substituted by dimethylamino; furfuryl or thienylmethyl; and $R_3$ is hydrogen, $C_1 \sim C_4$-alkyl, cyanomethyl, methoxycarbonylmethyl or 1-(propoxycarbonyl)ethyl.

2. A compound of claim 1 wherein
X is oxygen,
$R_1$ is 3-pyridyl or 4-pyridyl, and
$R_2$ is (1) benzyl, or (2) cycloalkyl, or (3) $C_4$ $C_6$-alkyl which may be substituted by halogen.

3. A compound of claim 2 wherein
X is oxygen,
$R_1$ is 3-pyridyl, and
$R_2$ is $C_4 \sim C_6$-alkyl or benzyl.

4. A compound of claim 3 wherein X is oxygen, $R_1$ is 3-pyridyl, $R_2$ is 3-methylbutyl, 3-methyl-2-butyl, 2-ethylbutyl, n-butyl or n-hexyl.

5. A compound of claim 1 wherein X is sulfur, $R_1$ is 3-pyridyl or 4-pyridyl, and $R_2$ is $C_4 \sim C_6$-alkyl or phenethyl.

6. A compound of claim 1 wherein X is sulfur, $R_1$ is 3-pyridyl, and $R_2$ is $C_4 \sim C_6$-alkyl.

7. A compound of claim 1 wherein X is

$R_1$ is 3-pyridyl or 4-pyridyl, and $R_2$ is $C_4 \sim C_6$-alkyl or benzyl, $R_3$ is hydrogen.

8. A compound of claim 1 wherein X is

—N—,
|
$R_3$ $R_1$ is 3-pyridyl, $R_2$ is $C_4 \sim C_6$-alkyl and $R_3$ is hydrogen.

9. A compound of claim 8 wherein X is

—N—,
|
$R_3$ $R_1$ is 3-pyridyl, $R_3$ is hydrogen, and $R_2$ is 3-methylbutyl, 2-methylbutyl or n-hexyl.

10. A bactericidal composition which comprises, as an effective component, a compound of the formula:

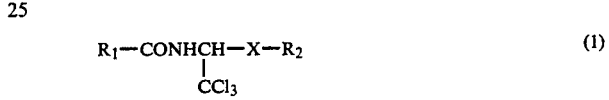

wherein

X is oxygen, sulfur or

—N—,
|
$R_3$ $R_1$ is 3-pyridyl or 4-pyridyl, $R_2$ is $C_1 \sim C_{12}$-alkyl; $C_3$ or $C_4$-alkenyl; $C_5$- or $C_6$-cycloalkyl which may be substituted by $C_1$- or $C_2$-alkyl; pyridyl; pyridylmethyl; phenethyl; cyano alkyl having one or two carbon atoms; methoxyethyl; 1-methoxymethyl-propyl; phenyl; phenyl which is substituted by one or more of $C_1 \sim C_4$-alkyl, $C_1 \sim C_4$-alkoxy, nitro, halogen, trifluoromethyl, allyl and methoxycarbonyl; benzyl; benzyl which is substituted by one or more of methyl, nitro methoxy or chloro; α-methylbenzyl; $C_1 \sim C_6$-alkyl which is substituted by halogen when X is oxygen or

—N—,
|
$R_3$ $C_2$- or $C_3$-alkyl which is substituted by dimethylamino; furfuryl or thienylmethyl; $R_3$ is hydrogen, $C_1 \sim C_4$-alkyl, cyanomethyl, methoxycarbonylmethyl or 1-propoxy carbonyl-ethyl and adjuvant(s).

11. A method for controlling bacteria on plants or in soil which comprises applying to said plants or soil a bactericidally effective amount of a compound of formula:

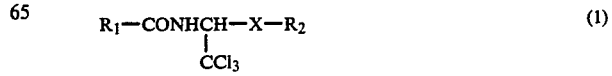

wherein

X is oxygen, sulfur or

$R_1$ is 3-pyridyl or 4-pyridyl, $R_2$ is $C_1\sim C_{12}$-alkyl, $C_3$- or $C_4$-alkenyl, $C_5$- or $C_6$-cycloalkyl which may be substituted by $C_1$- or $C_2$-alkyl; pyridyl; pyridylmethyl; phenethyl, cyano alkyl having one or two carbon atoms; methoxymethyl; 1-methoxymethyl-propyl; phenyl; phenyl which is substituted by one or more of $C_1\sim C_4$-alkyl, $C_1\sim C_4$-alkoxy, nitro, halogen, trifluoromethyl, allyl and methoxycarbonyl; benzyl; benzyl which is substituted by one or more of methyl, nitro, methoxy or chloro; α-methylbenzyl; $C_1\sim C_6$-alkyl which is substituted by halogen when X is oxygen or

$C_2$- or $C_3$-alkyl which is substituted by dimethylamino; furfuryl or thienylmethyl, and $R_3$ is hydrogen, $C_1\sim C_4$-alkyl, cyanomethyl, methoxycarbonylmethyl or 1-propoxycarbonyl-ethyl.

* * * * *